US009989499B2

(12) United States Patent
Moakler

(10) Patent No.: US 9,989,499 B2
(45) Date of Patent: Jun. 5, 2018

(54) DETECTING DAMAGE IN AN OILFIELD MIXING DEVICE

(71) Applicant: Schlumberger Technology Corporation, Sugar Land, TX (US)

(72) Inventor: Dean Moakler, Von Ormy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 113 days.

(21) Appl. No.: 14/700,782

(22) Filed: Apr. 30, 2015

(65) Prior Publication Data

US 2016/0320347 A1 Nov. 3, 2016

(51) Int. Cl.
*G01M 13/00* (2006.01)
*G01N 29/46* (2006.01)
*E21B 21/06* (2006.01)
*G01H 1/00* (2006.01)
*G01N 29/14* (2006.01)

(52) U.S. Cl.
CPC ........... *G01N 29/14* (2013.01); *E21B 21/062* (2013.01); *G01H 1/003* (2013.01); *G01M 13/00* (2013.01); *G01N 29/46* (2013.01); *G01N 2291/015* (2013.01); *G01N 2291/0258* (2013.01)

(58) Field of Classification Search
CPC .................. G01N 29/14; G01N 29/46; G01N 2291/0258; G01N 2291/015; G01H 1/003; G01M 13/00; E21B 21/062
USPC .......................................................... 73/579
See application file for complete search history.

(56) References Cited

U.S. PATENT DOCUMENTS

| 4,453,829 | A | * | 6/1984 | Althouse, III | .......... B01F 5/226 366/13 |
| 4,671,665 | A | * | 6/1987 | McIntire | ................. B01F 5/226 366/164.6 |
| 5,215,763 | A | | 6/1993 | Mattera | |
| 6,267,013 | B1 | * | 7/2001 | Stark | ......................... G01F 1/10 73/861.77 |
| 6,434,512 | B1 | * | 8/2002 | Discenzo | ................ F16C 19/52 702/184 |
| 6,491,422 | B1 | | 12/2002 | Rutten et al. | |
| 6,802,221 | B2 | * | 10/2004 | Hedeen | ............... G01M 13/045 73/587 |
| 8,545,091 | B1 | * | 10/2013 | Arribau | ..................... B01F 5/22 366/167.2 |
| 9,168,496 | B2 | * | 10/2015 | Arribau | ..................... B01F 5/22 |
| 9,375,691 | B2 | * | 6/2016 | Stegemoeller | ...... B01F 15/0227 |
| 9,804,051 | B2 | | 10/2017 | Moakler et al. | |
| 2004/0194539 | A1 | | 10/2004 | Gysling | |
| 2006/0152998 | A1 | | 7/2006 | Burr et al. | |
| 2008/0084783 | A1 | * | 4/2008 | Mazrooee | ............. B01F 3/1221 366/2 |

(Continued)

OTHER PUBLICATIONS

International Search Report and Written Opinion issued in International Patent Application No. PCT/US2016/013819 dated May 24, 2016; 10 pages.

*Primary Examiner* — J M Saint Surin
(74) *Attorney, Agent, or Firm* — Rachel E. Greene; Michael L. Flynn

(57) ABSTRACT

Information relating to vibration of a rotating component of an oilfield mixing device is obtained. The oilfield mixing device is operable to blend oilfield materials while the rotating component rotates. Damage sustained by the rotating component is then determined based on the obtained information.

17 Claims, 5 Drawing Sheets

(56) References Cited

U.S. PATENT DOCUMENTS

| | | |
|---|---|---|
| 2008/0141780 A1 | 6/2008 | Wavering et al. |
| 2008/0210212 A1 | 9/2008 | Baratta |
| 2010/0254212 A1 | 10/2010 | Howe et al. |
| 2014/0069650 A1 | 3/2014 | Stegemoeller et al. |
| 2015/0027702 A1 | 1/2015 | Godoy-Vargas et al. |
| 2015/0060072 A1 | 3/2015 | Busby et al. |

\* cited by examiner

DETECTING DAMAGE IN AN OILFIELD MIXING DEVICE

BACKGROUND OF THE DISCLOSURE

In some oilfield operations, solid particles are mixed with a fluid using an oilfield mixing device. For example, sand, sand-like ceramics, and/or other solid particles may be blended or otherwise mixed with a fluid composition, gel, water, and/or other fluids. As the solid particles and the fluid are mixed, the resulting solid/fluid mixture, sometimes referred to as a slurry, is pressurized and forced out through an outlet in the oilfield mixing device.

During operation of the oilfield mixing device, the solid particles flow out of a hopper in a substantially continuous stream and drop onto a rotating slinger through an upper inlet opening in a casing that houses the slinger. An impeller, which is connected with and rotates at the same speed as the slinger, creates air suction that draws the fluid into the casing through a lower inlet opening. As the fluid is pulled into the casing, it is pressurized by the impeller and mixed with the solid particles, which are being flung radially outwards from the slinger in a centrifugal action. The solid/fluid mixture is then continuously discharged, under pressure, through an outlet in the casing.

Due to the abrasive properties of certain solid particles, portions of the oilfield mixing device that are exposed to the solid particles and/or the solid/fluid mixture may be eroded during mixing operations, thus, reducing the life cycle of the oilfield mixing device. Other damage, such as chipping, cracking, and/or breaking of components of the oilfield mixing device may also be sustained. Such damage results in failure of the oilfield mixing device during mixing operations, which may also damage and other equipment communicably coupled to the oilfield mixing device. Interruptions in mixing operations may also reduce the success and/or efficiency of certain downhole operations, which may reduce hydrocarbon production of a well. In some instances, the downhole operations may have to be repeated, thus increasing costs and delaying production.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces an apparatus that includes a system operable to indicate that damage has been sustained by a rotating component of an oilfield mixing device that is operable for blending oilfield materials. The system includes a sensor connected with the oilfield mixing device and operable to generate information related to vibration of the rotating component. The system also includes a monitoring device in communication with the sensor and operable to determine an amplitude of the generated information.

The present disclosure also introduces a method that includes obtaining information relating to vibration of a rotating component of an oilfield mixing device. The oilfield mixing device is operable to blend oilfield materials while the rotating component rotates. The method also includes detecting damage sustained by the rotating component based on the obtained information.

The present disclosure also introduces a method that includes detecting vibrations generated by rotating components of an oilfield mixing device. The detected vibrations are associated with corresponding ones of the rotating components based on corresponding frequencies of the detected vibrations. An amplitude of the detected vibrations is determined at one of the frequencies corresponding to a selected one of the rotating components. Damage sustained by the selected one of the rotating components is determined based on the determined amplitude.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
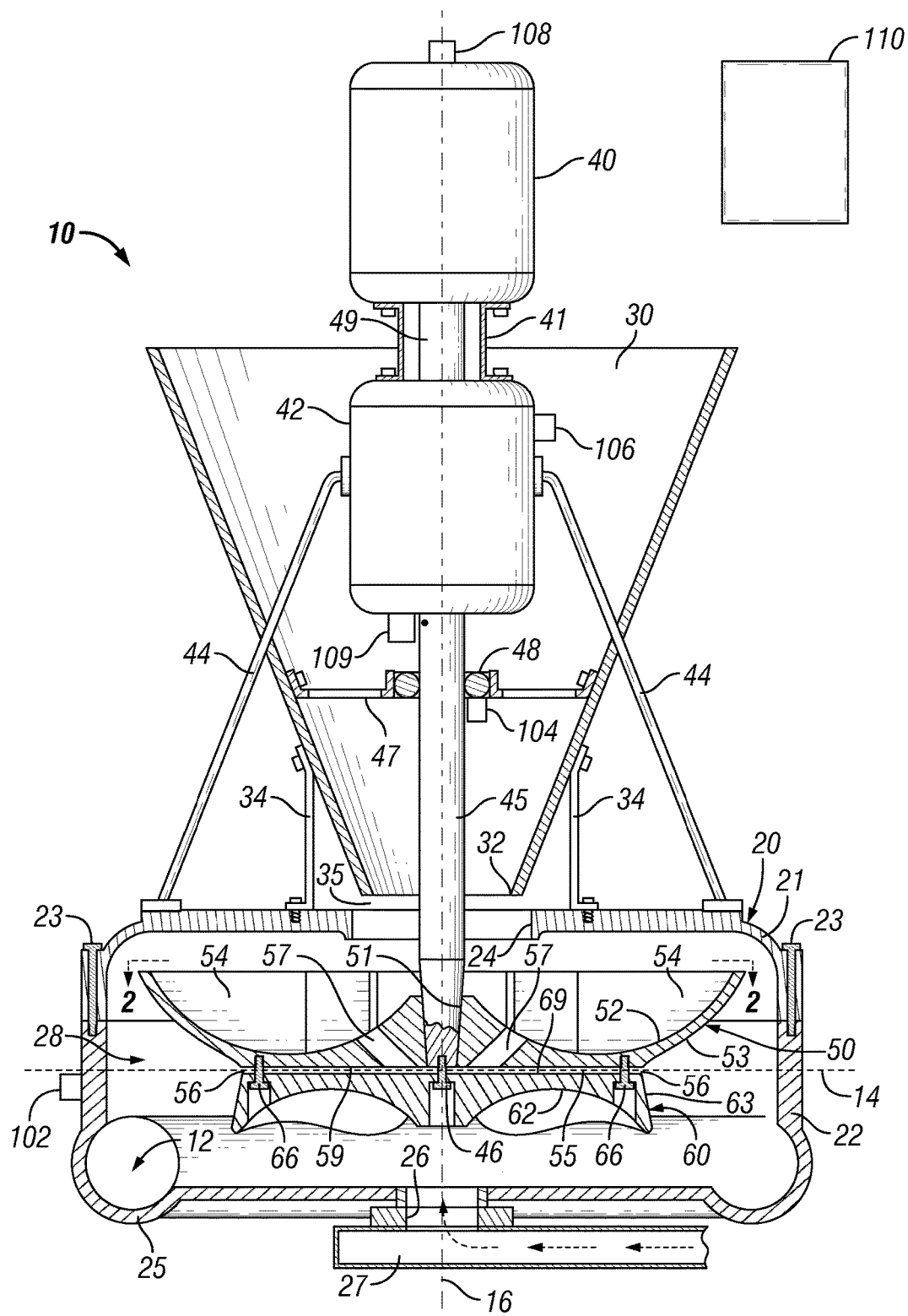
FIG. 1 is a sectional side view of at least a portion of apparatus related to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

During the operational life of an oilfield mixing device or other oilfield device comprising rotating components, a component of the device may be progressively worn, eroded, or otherwise damaged, such as may result in loss of mass by the component and/or otherwise cause the component to become unbalanced. Such damage may be caused by, for example, particulate material like sand, ceramics, proppants, and/or other solid particles repeatedly impinging upon the component during mixing operations. The amount of damage sustained by the components may be determined by measuring the vibration generated or caused by the damaged component due to the loss of mass and/or balance. By measuring or monitoring such vibration, damage sustained by the component and/or the remaining functional life of the component may be determined.

FIG. 1 is a sectional side view of a portion of apparatus related to one or more aspects of the present disclosure. The depicted apparatus is an example oilfield mixing device 10 implemented as a vortex mixer comprising components that may be progressively worn or eroded by solid particles during mixing operations.

The oilfield mixing device 10 comprises a hopper 30, such as may contain solid particles (not shown) like sand, ceramic particles, propping agents, and/or other solid particles. The oilfield mixing device 10 further comprises a casing 20 (i.e., a housing) having a generally cylindrical shape defining an internal chamber 28, such as may receive therein the solid particles from the hopper 30 and a fluid (not shown) through an inlet 26 from a conduit 27. The solid particles and fluid are mixed in the casing 20 to form a solid/fluid mixture or "slurry" (not shown).

The casing 20 may comprise an upper section 21 coupled with a lower section 22, such as via one or more threaded fasteners 23 and/or other means. The hopper 30 is mounted above the casing 20 by one or more vertical supports 34. The bottom end of the hopper 30 comprises an outlet opening 32 that terminates at or just above an inlet opening 24 of the casing 20, such as in a manner permitting solid particles to be continuously dropped from the hopper 30 into the chamber 28.

Disposing the outlet opening 32 of the hopper 30 just above the inlet opening 24 of the casing may provide an exterior air exhaust space 35 between the hopper 30 and the inlet opening 24, such as may permit air or other gasses located between and/or within the solid particles to vent from the casing 20. However, the ability to vent air or other gasses out of the casing 20 may be provided by other means, such as a vent tube (not shown) that may extend through the wall of the hopper 30 and downward through the inlet opening 24. When such venting means are utilized, the hopper 30 may abut against the inlet opening 24, such that the exhaust space 35 is minimized or eliminated.

A drive shaft extension 45 extends into the chamber 28 through the inlet opening 24 in the upper section 21 of the casing 20. The drive shaft extension 45 may be maintained in position with respect to the inlet opening 24 and the outlet opening 32 by a bearing 48, such as a ball bearing, extending about the drive shaft extension 45. The bearing 48 may be held in place within the hopper 30 by a lateral support member 47. The drive shaft extension 45 is driven by a prime mover 40, such as an electric motor, a hydraulic motor, a pneumatic motor, an engine, or another type of rotary drive operatively coupled with the drive shaft extension 45. The oilfield mixing device 10 may further comprise a gear box 42 operatively coupled between a drive shaft 49 of the prime mover 40 and the drive shaft extension 45. The gear box 42 may be or comprise a transmission or a gear train, such as may be operable to increase or decrease the speed at which the prime mover 40 rotates the drive shaft extension 45 and the components coupled with the drive shaft extension 45. The gear box 42 and/or the prime mover 40 may be coupled together by a coupling 41 and maintained in position by one or more vertical supports 44, which may be fastened to the upper section 21 of the casing 20 and/or to other portions of the oilfield mixing device 10.

Figure 2:
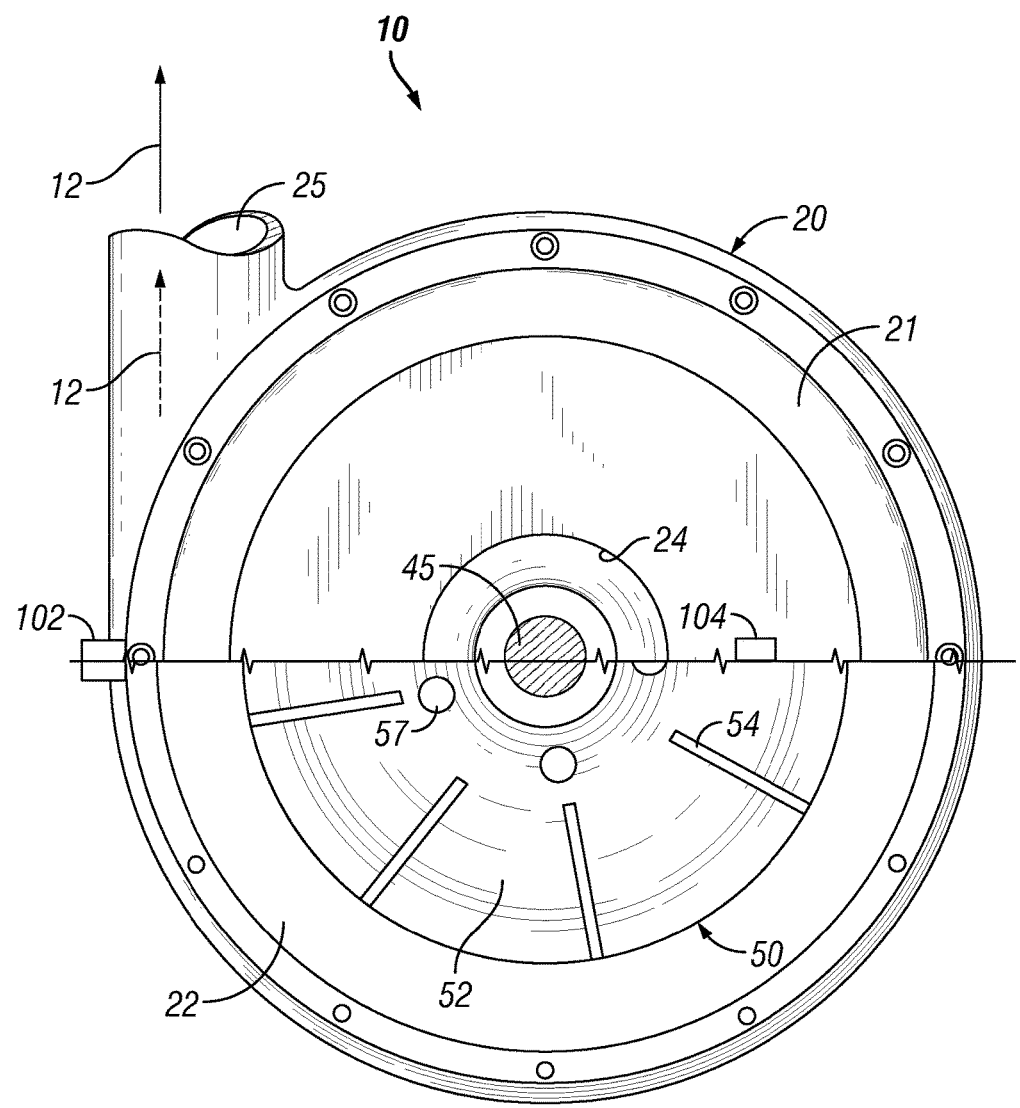
FIG. 2 is a partial sectional view of a portion of the apparatus shown in FIG. 1.

FIG. 2 is a top, partial-sectional view of a portion of an implementation of the oilfield mixing device 10 shown in FIG. 1. Referring collectively to FIGS. 1 and 2, the oilfield mixing device 10 further comprises a slinger 50 and an impeller 60 disposed within the casing 20. An upper surface 52 of the slinger 50 may have a toroidal concave configuration facing the upper section 21 of the casing 20. The concave surface 52 of the slinger 50 may comprise a plurality of upstanding, radially outwardly extending blade members 54. The bottom side of the slinger 50 may comprise a flat or otherwise shaped face 59, which may match a corresponding flat or otherwise shaped face 69 on the upper side of the impeller 60. The slinger 50 may be coupled or otherwise fixedly connected to the impeller 60 to rotate synchronously therewith. For example, the slinger 50 and the impeller 60 may be coupled at their respective faces 59, 69 by one or more threaded fasteners 66 and/or other means. The slinger 50 and the impeller 60 are shown axially spaced apart, such as to define an exhaust space 55 between the face 59 of the slinger 50 and the face 69 of the impeller 60. The exhaust space 55 may be operable to exhaust gas therethrough, and a radially outer portion 56 of the exhaust space 55 may be operable as an air or gas inlet into the exhaust space 55. The slinger 50 may further comprise exhaust channels 57, which may extend diagonally or otherwise through the body of the slinger 50. The slinger 50 may further comprise an outer side 53 having a radially inward downward sloping surface, which terminates at the gas inlet 56, located at the radially inward portions of the outer side 53. The impeller 60 may comprise a concave inner surface 62 having a vortex configuration that faces toward the lower section 22 of the casing 20, such that rotation of the impeller 60 may induce air on the underside thereof to move in a vortex manner. An outer side 63 of the impeller may be a radially outward downward sloping surface.

The slinger 50 may further comprise a central opening 51 extending therethrough, such as to receive therein or therethrough the bottom end of the drive shaft extension 45. The impeller 60 may be secured to the bottom end of drive shaft extension 45 by one or more threaded fasteners 46 and/or other means, such as may extend through a central portion of the impeller 60 to threadedly engage the drive shaft extension 45 and retain the impeller 60 in connection with the drive shaft extension 45. The slinger 50 and the impeller 60 may thus be coupled to the drive shaft extension 45 and, therefore, the gear box 42 and the prime mover 40.

The lower section 22 of the casing 20 comprises an outlet 25 extending therefrom, such as may be operable for discharging the solid/fluid mixture from the casing 20. The outlet 25 may be positioned adjacent the bottom and radially outward portion of the lower section 22, and may comprise a substantially tubular configuration, whether substantially cylindrical or otherwise. The lower section 22 of the casing 20 may further comprise the inlet opening 26 at the axial center of the casing 20. The inlet opening 26 may be fluidly connected with the inlet conduit 27, which may be in connection with a source of fluid (not shown).

During mixing operations performed by the oilfield mixing device 10, the solid particles contained in the hopper 30 are mixed with the fluid entering the inlet opening 26 to obtain a solid/fluid mixture. At the start of the oilfield mixing operations, the prime mover 40 rotates the drive shaft extension 45 and, therefore, the slinger 50 and the impeller 60. With the slinger 50 and the impeller 60 in motion, a selected amount of solid particle material may be loaded into the hopper 30 such that the solid particle material may flow in a substantially continuous stream through the inlet opening 24 and drop onto the rotating slinger 50. As the solid particle material drops onto the slinger 50, the solid particle material is continuously propelled radially outward while contacting and/or sliding along the concave surface 52 and the blade members 54 of the slinger 50. Such contact wears and/or erodes portions of the slinger 50, such as the concave surface 52 and the blade members 54.

With the impeller 60 rotating at the same speed as the slinger 50, the vortex action of the impeller 60 generates a suction force above the inlet opening 26, thereby drawing the fluid from the inlet conduit 27 into the casing 20 though the inlet opening 26, at which time the impeller 60 propels the fluid radially outward. Thus, the fluid is pressurized by the impeller 60 and mixed with the solid particles. The result is a thorough mixing of the solid particles and the fluid to form a solid/fluid mixture, which may be continuously discharged under pressure through the outlet 25, as shown by arrows 12. From the outlet 25, the solid/fluid mixture may be carried into a storage unit (not shown) or a pumper unit (not shown) for injection into a wellbore (not shown).

Figure 3:
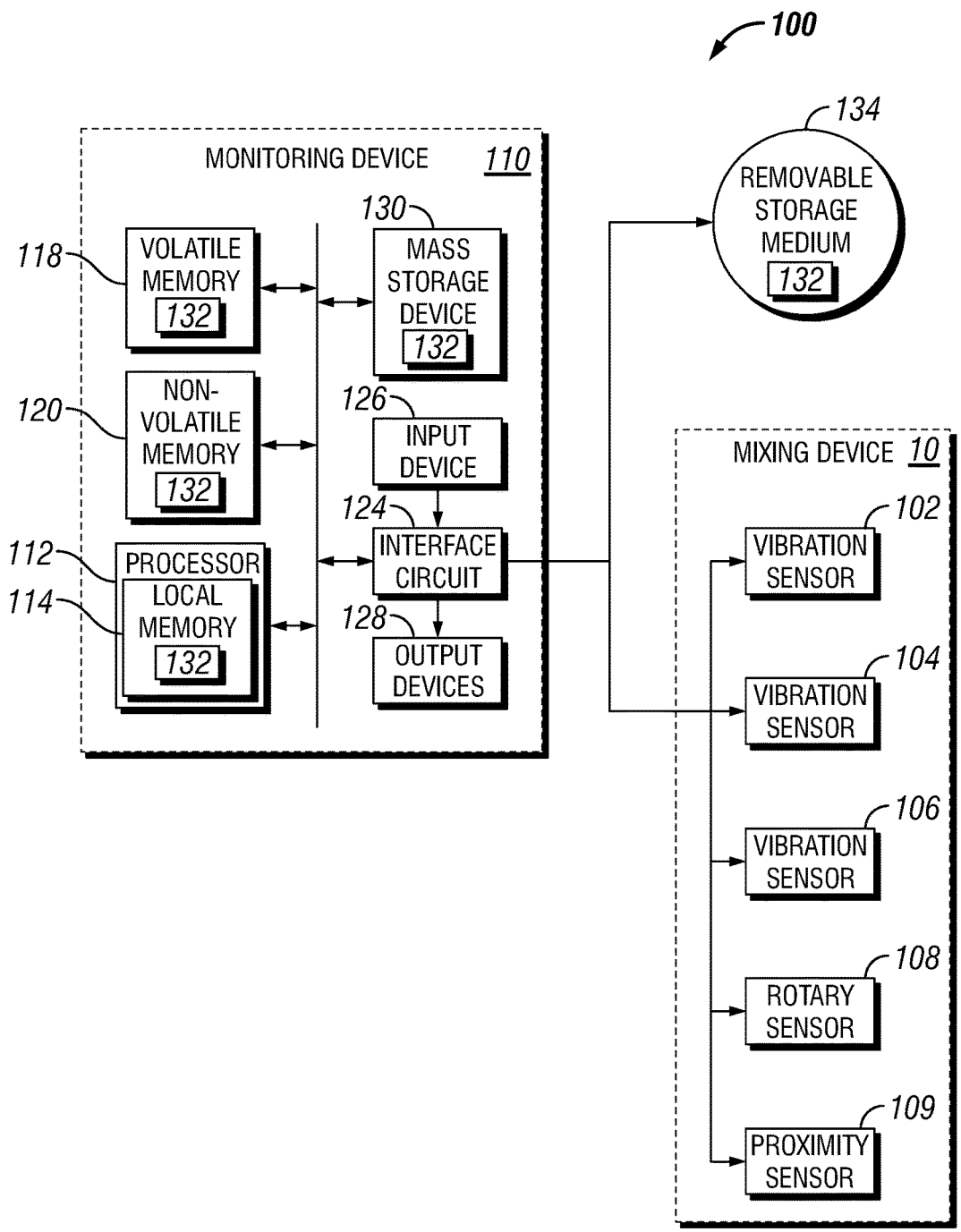
FIG. 3 is a schematic view of at least a portion of apparatus according to one or more aspects of the present disclosure.

FIG. 3 is a schematic view of a portion of an example implementation of a monitoring system 100 according to one or more aspects of the present disclosure. The monitoring system 100 may be utilized to determine and/or indicate damage to one or more components of the oilfield mixing device 10. The following description refers to FIGS. 1-3, collectively.

The monitoring system 100 may comprise one or more sensors operable to generate signals or information relating to operational parameters of the oilfield mixing device 10. The one or more sensors may comprise one or more vibration sensors 102, 104, 106, which may be operable to generate signals and/or information relating to vibration, acceleration, and/or shock generated or caused by various components of the oilfield mixing device 10 during mixing operations, such as when the slinger 50, impeller 60, drive shaft extension 45, bearing 48, and/or gear box 42 are rotating. The vibration sensors 102, 104, 106 may be mounted directly on the oilfield mixing device 10, which may permit the information relating to vibration to be generated via direct contact with the oilfield mixing device 10 during monitoring operations. For example, the first vibration sensor 102 may be mounted to a side surface of the lower section 22 of the casing 20, the second vibration sensor 104 may be mounted to an upper surface of the upper section 21 of the casing 20, and the third vibration sensor 106 may be mounted to the gear box 42. However, other types, numbers, and/or locations of sensors are also within the scope of the present disclosure.

During operations of the oilfield mixing device 10, vibrations generated and/or caused by certain components of the oilfield mixing device 10 may be transmitted to the vibration sensors 102, 104, 106. For example, vibrations generated by the slinger 50, blade members 54, impeller 60, and bearings 48 may be transmitted to the vibration sensors 102, 104, 106 via the drive shaft extension 45, the gear box 42, the hopper 30, the vertical supports 34, 44, and/or the casing 20. Vibrations generated by the gear box 42 or components of the gear box 42 may be detected by the third vibration sensor 106 and/or transmitted to the other vibration sensors 102, 104 via the hopper 30, the vertical supports 34, 44, and/or the casing 20. Accordingly, the vibration sensors 102, 104, 106 may generate information relating to vibration generated or caused by the slinger 50, the blade members 54, the impeller 60, the bearings 48, and the gear box 42 without direct contact between the vibration sensors 102, 104, 106 and these components.

The vibration sensors 102, 104, 106 may comprise one, two, or three-axis accelerometers disposed to detect vibrations along one or more axes, perhaps including an axis that is substantially parallel to a lateral axis 14 of the oilfield mixing device 10 that extends substantially perpendicular to an axis of rotation 16 about which the drive shaft extension 45, the slinger 50, and the impeller 60. However, other arrangements are also within the scope of the present disclosure.

The one or more sensors of the monitoring system 100 may also comprise one or more rotary sensors 108 operable to detect angular phase and/or rotational speed of one or more rotating components of the oilfield mixing device 10, such as the prime mover 40, the drive shaft 49, the gear box 42, the drive shaft extension 45, the bearing 48, the slinger 50, and/or the impeller 60, and output electrical signals comprising information relating to the angular phase and/or speed. The phase and/or speed information may be utilized to determine the angular location of damage to one or more of the rotating components, and/or to determine one or more harmonic frequencies of one or more of the rotating components. For example, as shown in the example implementation depicted in FIG. 1, a rotary sensor 108 may be coupled with or disposed in association with the prime mover 40 in a manner permitting the rotary sensor 108 to detect the angular phase and/or speed of the drive shaft 49 extending from the prime mover 40. However, other numbers and/or locations of the rotary sensors 108 are also within the scope of the present disclosure. Each rotary sensor 108 may be or comprise an encoder, a rotary potentiometer, a synchro, a resolver, and/or a rotary variable differential transformer (RVDT), among other examples within the scope of the present disclosure.

Information relating to angular phase and/or rotational speed of one or more of the rotating components of the oilfield mixing device 10 may also or instead be generated by one or more proximity sensors 109 coupled with or disposed in association with one or more components of the oilfield mixing device 10. That is, the proximity sensors 109 may be operable to convert position or presence of a moving or rotating component of the oilfield mixing device 10 to an electrical signal comprising information relating to angular phase and/or rotational speed. For example, a proximity sensor 109 may be coupled to or otherwise disposed adjacent the drive shaft 49, the gear box 42, the drive shaft extension 45, and/or another rotating component of the oilfield mixing device 10, such as may be permit the proximity sensor 109 to detect the presence and/or movement of a reference point along the drive shaft extension 45, drive shaft 49, and/or another rotating component of the oilfield mixing device 10 to generate information relating to angular phase and/or rotational speed. In the example implementation depicted in FIG. 1, a proximity sensor 109 is coupled with the gear box 42 adjacent or proximate the drive shaft extension 45 in a manner permitting the proximity sensor 109 to detect information indicative of the angular phase and/or speed of the drive shaft extension 45. However, other numbers and/or locations of the proximity sensors 109 are also within the scope of the present disclosure. Each proximity sensors 109 may be or comprise a linear encoder, a capacitive sensor, an inductive sensor, a magnetic sensor, a Hall effect sensor, and/or a reed switch, among other examples within the scope of the present disclosure.

The monitoring system 100 may also comprise a monitoring device 110 in communication with the sensors 102, 104, 106, 108, 109. Such communication may be via wired and/or wireless connections. However, for clarity and ease of understanding, such connections are not depicted in FIG. 1, and a person having ordinary skill in the art will appreciate that myriad means for such connections are within the scope of the present disclosure.

FIG. 3 further shows a schematic view of at least a portion of an example implementation of the monitoring device 110 according to one or more aspects of the present disclosure. The monitoring device 110 may be operable to execute example machine-readable instructions to implement at least a portion of one or more of the methods and/or processes described herein, and/or to implement a portion of one or more of the example oilfield devices described herein. The monitoring device 110 may be or comprise, for example, one or more processors, special-purpose computing devices, servers, personal computers, personal digital assistant ("PDA") devices, smartphones, internet appliances, and/or other types of computing devices.

The monitoring device 110, may be further operable to receive the information relating to vibration (hereafter "vibration information") generated by the one or more vibration sensors 102, 104, 106, as described above, and convert the vibration information from a time domain to a frequency domain. The monitoring device 110 may transform the vibration information from the time domain to the frequency domain utilizing one or more known or future-developed mathematical transforms. Such transforms may include a Continuous Fourier transform, a Discrete Fast Fourier transform, a Hilbert transform, a Laplace transform, and/or a Maximum Entropy Method, among other examples within the scope of the present disclosure. The monitoring device 110 may be operable to utilize the one or more transforms to perform time domain to frequency domain transformation described above. Thus, for example, the monitoring device 110 may be or comprise a spectrum analyzer operable to convert the vibration information from the time domain to the frequency domain and determine power or amplitude of the vibration information at selected frequencies along a frequency spectrum, including harmonic frequencies.

The monitoring device 110 may comprise a processor 112, such as a general-purpose programmable processor. The processor 112 may comprise a local memory 114, and may execute coded instructions 132 present in the local memory 114 and/or another memory device. The processor 112 may execute, among other things, machine-readable instructions or programs to implement the methods and/or processes described herein. The programs stored in the local memory 114 may include program instructions or computer program code 132 that, when executed by the processor 112, cause the monitoring system 100 to perform tasks as described herein, including converting the vibration information from the time domain to the frequency domain and determining the amplitude of the vibration information. The program instructions or computer program code 132, when executed by the processor 112, may also cause the monitoring system 100 to determine the existence and perhaps location of wear, erosion, and/or other damage sustained by one or more components of the oilfield mixing device 10, the amount of such wear, erosion, and/or other damage, and/or the amount of functional life remaining in the one or more components of the oilfield mixing device 10.

The processor 112 may be, comprise, or be implemented by one or a plurality of processors of various types suitable to the local application environment, and may include one or more of general-purpose computers, special-purpose computers, microprocessors, digital signal processors ("DSPs"), field-programmable gate arrays ("FPGAs"), application-specific integrated circuits ("ASICs"), and processors based on a multi-core processor architecture, as non-limiting examples. Of course, other processors from other families are also appropriate.

The processor 112 may be in communication with a main memory, such as may include a volatile memory 118 and a non-volatile memory 120, perhaps via a bus 122 and/or other communication means. The volatile memory 118 may be, comprise, or be implemented by random access memory (RAM), static random access memory (SRAM), synchronous dynamic random access memory (SDRAM), dynamic random access memory (DRAM), RAMBUS dynamic random access memory (RDRAM), and/or other types of random access memory devices. The non-volatile memory 120 may be, comprise, or be implemented by read-only memory, flash memory, and/or other types of memory devices. One or more memory controllers (not shown) may control access to the volatile memory 118 and/or the non-volatile memory 120. The processor 112 may be further operable to cause the monitoring device 110 to receive, collect, and/or record the signals and/or other information generated by the rotary sensors 108, the proximity sensors 109, the vibration sensors 102, 104, 106, and/or other sensors onto the main memory.

The monitoring device 110 may also comprise an interface circuit 124. The interface circuit 124 may be, comprise, or be implemented by various types of standard interfaces, such as an Ethernet interface, a universal serial bus (USB), a third generation input/output (3GIO) interface, a wireless interface, and/or a cellular interface, among others. The interface circuit 124 may also comprise a graphics driver card. The interface circuit 124 may also comprise a communication device, such as a modem or network interface card, such as to facilitate exchange of data with external computing devices via a network (e.g., Ethernet connection, digital subscriber line ("DSL"), a telephone line, a coaxial cable, a cellular telephone system, a satellite, etc.). The sensors 102, 104, 106, 108, 109 may be connected with the monitoring device 110 via the interface circuit 124, such as may facilitate communication between the sensors 102, 104, 106, 108, 109 and the monitoring device 110.

One or more input devices 126 may also be connected to the interface circuit 124. The input devices 126 may permit an operator to enter data and commands into the processor 112, such as the selected or predetermined phase, speed, flow, and/or pressure parameters described herein. The input devices 126 may be, comprise, or be implemented by a keyboard, a mouse, a touchscreen, a track-pad, a trackball, an isopoint, and/or a voice recognition system, among other examples. One or more output devices 128 may also be connected to the interface circuit 124, such as to display the vibration information, whether in the time domain or the frequency domain. The output devices 128 may be, comprise, or be implemented by display devices (e.g., a liquid crystal display (LCD) or cathode ray tube display (CRT), among others), printers, and/or speakers, among other examples.

The monitoring device 110 may also comprise one or more mass storage devices 130 and/or a removable storage medium 134, such as may be or include floppy disk drives, hard drive disks, compact disk (CD) drives, digital versatile disk (DVD) drives, and/or USB flash drives, among other examples. The information generated by the rotary sensors 108, the proximity sensors 109, the vibration sensors 102, 104, 106, and/or other sensors may be stored on the one or more mass storage devices 130 and/or the removable storage medium 134.

The coded instructions 132 may be stored in the mass storage device 130, the volatile memory 118, the non-volatile memory 120, the local memory 114, and/or the removable storage medium 134. Thus, the modules and/or other components of the monitoring device 110 may be implemented in accordance with hardware (embodied in one or more chips including an integrated circuit, such as an application specific integrated circuit), or may be implemented as software or firmware for execution by one or more processors. In the case of firmware or software, the implementation may be provided as a computer program product including a computer readable medium or storage structure embodying computer program code (i.e., software or firmware) thereon for execution by the processor 112.

As stated above, portions or components of the oilfield mixing device 10 may be chipped, broken off, worn, eroded, and/or otherwise damaged during mixing or other operations, resulting in loss of mass by the component. Accordingly, the damaged component of the oilfield mixing device 10 may become unbalanced, causing it to vibrate during rotation. The vibrations generated by the damaged component may be monitored by the vibration sensors 102, 104, 106, measured, and/or recorded. The vibration information generated by the vibration sensors 102, 104, 106 may be indicative of or otherwise utilized to determine and/or estimate the amount of damage sustained by one or more components of the oilfield mixing device 10. Based on the amount of damage, the amount of remaining life of the component and/or the oilfield mixing device 10 may be determined and/or estimated.

To determine the relationship between vibration and damage to one or more components of the oilfield mixing device 10, an experiment was conducted on four used slingers (not shown), each having a configuration similar to the slinger 50 shown in FIGS. 1 and 2. Each slinger comprised a steel construction, had a radius of 10.75 inches, and comprised a urethane coating. Each slinger had sustained a different amount of damage caused by erosion in response to repeated impingement of the above-described solid particle material during oilfield mixing operations. An unused slinger was also tested to generate baseline vibration measurements for comparison with the vibration measurements generated by the used slingers.

The experiment comprised coupling each slinger to an electric motor and rotating each slinger (individually) for about 160 seconds at about 455 RPM. A vibration sensor and a rotary sensor were coupled to the electric motor for generating information relating to vibration, angular phase, and rotational speed of the slinger. The vibration and rotary sensors were connected in communication with a monitoring device. The vibration sensor, the rotary sensor, and the monitoring device utilized in the experiment comprised the same or similar structure and/or function as the vibration sensors 102, 104, 106, the rotary sensors 108, and the monitoring device 110 described above. The experimental parameters, results, and descriptions of the condition for the slingers are set forth below in Table 1.

TABLE 1

| Sample | Imbalance (g) | Centrifugal Force (lb-force) | Condition of Slinger |
|---|---|---|---|
| D | 30.8 | 40.64 | Coating delaminated on multiple blades. |
| C | 66.1 | 87.21 | Coating delaminated on one blade. |
| B | 225.6 | 297.65 | Coating had 80% life remaining. |
| A | 608.0 | 802.18 | Coating partially peeled; zero life remaining. |

The column labeled "Sample" identifies each of the four urethane coated slingers A through D. The column labeled "Imbalance" lists the corresponding vibration information generated by the vibration sensor, shown in G-force units. The vibration information is listed in order from lowest to highest. A relationship may be seen between the level or amplitude of vibration and the condition of the slingers. That is, the slingers that were less eroded and/or damaged generated lower G-force amplitudes, while the slingers that were more eroded and/or damaged generated greater G-force amplitudes.

Since wear and/or erosion of the slinger often occurs more on one side of the slinger than another (in a radial direction), the amount of wear and/or erosion may be detected based on the amplitude of the imbalance caused by the loss of mass due to wear and/or erosion. During the course of the experiment, each of the slingers was also balanced to specifications of a new slinger. Using the specifications, an amount of additional mass to facilitate balancing of each of the five slingers was determined. Using the determined additional mass, the radius of the slingers, and the rotational speed of the slingers during the experiment, a resulting centrifugal force for each slinger was determined. In Table 1, the centrifugal force is shown in lb-force units in the column labeled "Centrifugal Force." As demonstrated in Table 1, a relationship may be seen between the amount or amplitude of centrifugal force and the condition of the slingers. That is, the slingers that were less worn and/or eroded were associated with smaller centrifugal forces, while the slingers that were more worn and/or eroded were associated with greater centrifugal forces. Therefore, based on the determined amplitudes of vibration generated or caused by the slinger, the amount of damage sustained by the slinger may be determined.

The above-described experiment was conducted utilizing a slinger removed from the oilfield mixing device to confirm that vibration information may be utilized to detect and estimate the extent of damage to a slinger. However, the monitoring system 100 shown in FIG. 3 may be utilized to detect and estimate the extent of damage to the slinger 50 while the slinger 50 remains assembled within the oilfield mixing device 10, as shown in FIGS. 1 and 2.

That is, when the components of the oilfield mixing device 10 are rotating, each of the rotating components vibrate at different frequencies. Such vibrations are transmitted to the vibration sensors 102, 104, 106, which generate vibration information generated or caused by the rotating components, and such vibration information is communicated to the monitoring device 110, as described above. To examine the integrity and/or damage of a specific rotating component of the oilfield mixing device 10, vibrations generated or caused by a selected rotating component may be isolated or otherwise identified by identifying the frequency at which the selected component vibrates, and the amplitude of the identified vibrations may then be determined.

Figure 4:
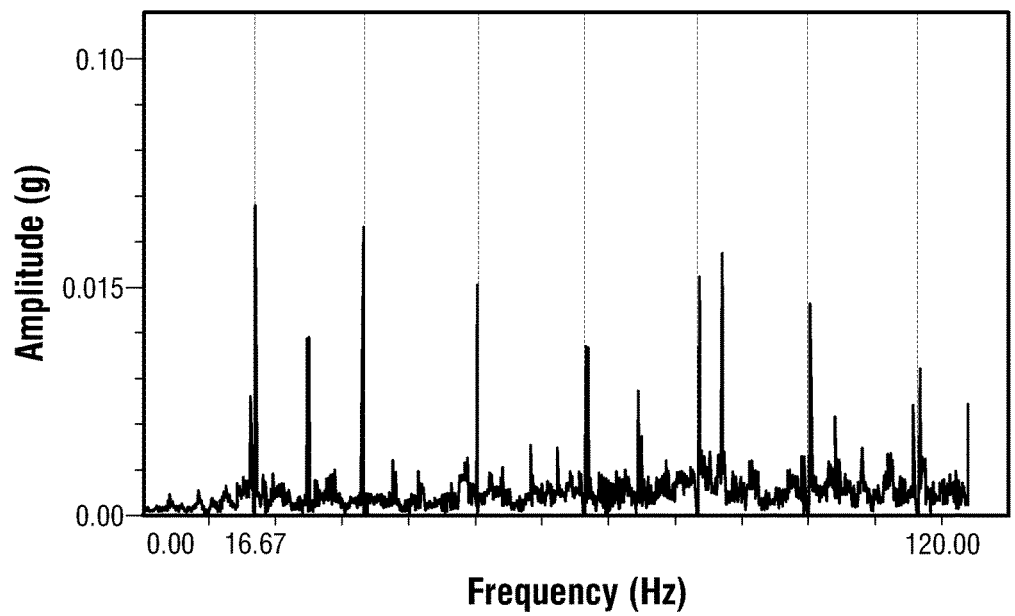
FIG. 4 is a graph related to one or more aspects of the present disclosure.
Figure 5:
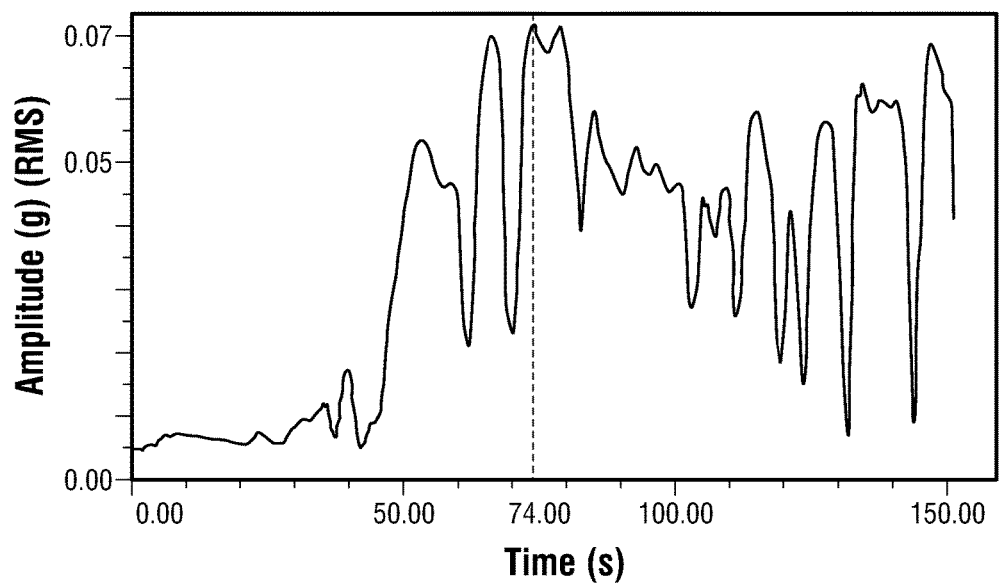
FIG. 5 is a graph related to one or more aspects of the present disclosure.

An experiment was conducted utilizing the oilfield mixing device 10 and the monitoring device 100, wherein the slinger 50 was rotated by the prime mover 40 at about 1000 RPM or 16.67 Hz. Since wear and/or erosion of the slinger often occurs more on one side of the slinger (in a radial direction), the imbalance caused by the wear and/or erosion resulted in the slinger 50 vibrating at its first harmonic frequency of about 16.67 Hz, which is equal to the rotational speed of the slinger 50. FIGS. 4 and 5 show graphs related to one or more aspects of the present disclosure. FIG. 4 shows the vibration information generated by one or more of the vibration sensors 102, 104, 106 in the frequency domain, wherein the horizontal axis is the frequency spectrum of the vibration information, shown in Hz, and the vertical axis is the amplitude of the vibration information, shown in G-units. After the frequency of vibration of the slinger 50 are determined (i.e., 16.67 Hz), the amplitude of the vibrations at the determined frequency may be determined, such as by examining the graph in FIG. 4 and/or another graph, chart, table, and/or other means for demonstrating the relationship between amplitude and frequency of vibration of the slinger 50.

FIG. 5 shows the vibration information at the harmonic frequency of the slinger 50 generated by one or more of the vibration sensors 102, 104, 106, wherein the horizontal axis denotes time in seconds and the vertical axis denotes the amplitude in G-units. The amplitude of the vibration information may be determined, for example, by examining the graph in FIG. 5 and/or another graph, chart, table, and/or other means for demonstrating the relationship between amplitude of the vibration of the slinger 50 at its first harmonic frequency, such as by selecting the maximum amplitude generated during monitoring operations, which is shown in FIG. 5 to occur at a time of about 74 seconds. Determining the amplitude of the vibration information may also include determining the average amplitude of the vibration information generated during the monitoring operations.

It is noted that the monitoring device 110 may generate either or both of the above-described demonstration means, such as the graphs shown in FIGS. 4 and 5. However, other devices may also be utilized to generate either or both of the demonstration means within the scope of the present disclosure.

The determined amplitude of the vibration information may be utilized to determine damage sustained by the slinger. The determined amplitude of the vibration information may also be compared to information relating to vibration generated by other used slingers rotating within other mixing devices, such as to determine a relative amount of wear, erosion, and/or other damage sustained by the slingers. The determined amplitude of the vibration information may also be compared to vibration information generated by an unused slinger, such as may be utilized as a baseline for determining the amount of wear, erosion, and/or other damage sustained by a used slinger. A database containing information relating to vibration generated by used and/or unused slingers may be compiled to create functional life profiles, which may be utilized to estimate the remaining functional life of a slinger.

The monitoring system 100 may also be utilized to detect damage sustained by one or more rotating components of the oilfield mixing device 10 other than or in addition to the slinger 50. That is, after the vibration frequency of a component is determined, the amplitude of the determined vibration may be determined and then utilized to determine and/or estimate the damage and/or the remaining functional life of the selected component. For example, the monitoring system may be utilized to detect and/or estimate damage sustained by the impeller 60, the bearing 48, one of more gears and/or other rotating components within the gear box 42, and/or other rotating components of the oilfield mixing device 10. The monitoring system 100 may also be utilized to detect and/or estimate damage or loosening of one or more threaded fasteners 23, 46, 66 of the oilfield mixing device 10. Such damage, in the context of the present disclosure, may include chipping, cracking, breaking, wear, and/or erosion of a component of the oilfield mixing device 10.

Figure 6:
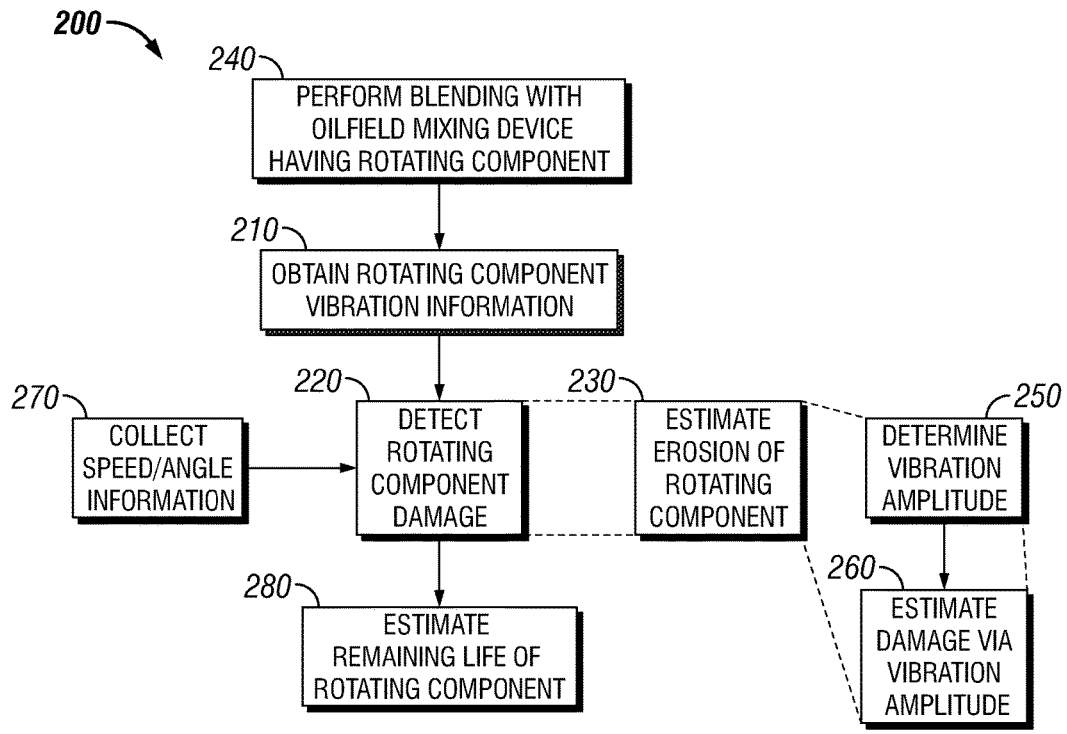
FIG. 6 is a flow-chart diagram of at least a portion of a method according to one or more aspects of the present disclosure.

FIG. 6 is a flow-chart diagram of at least a portion of an example implementation of a method (200) according to one or more aspects of the present disclosure. The method (200) may be performed utilizing at least a portion of one or more implementations of the apparatus shown in one or more of FIGS. 1-3 and/or other apparatus within the scope of the present disclosure.

The method (200) comprises obtaining (210) information relating to vibration of a rotating component of an oilfield mixing device. One or more aspects of the oilfield mixing device may be at least similar to those of the oilfield mixing device 10 shown in FIGS. 1 and 2, among other oilfield mixing devices within the scope of the present disclosure. For example, the rotating component be at least similar in function and/or structure to the slinger 50, the impeller 60, the drive shaft extension 45, the gear box 42 or a component thereof, the drive shaft 49, and/or the prime mover 40 shown in FIGS. 1 and 2, among other examples of rotating components within the scope of the present disclosure. Obtaining (210) the vibration information may utilize apparatus that may be at least similar to one of more of the sensors 102, 104, 106, 108, 109, one or more components of the monitoring device 110, and/or other components of the monitoring system 100 shown in FIGS. 1 and 3, among other examples within the scope of the present disclosure.

The method (200) also comprises detecting (220) damage sustained by the rotating component based on the obtained (210) vibration information. For example, detecting (220) the damage sustained by the rotating component may include estimating (230) an amount of erosion sustained by the rotating component based on the obtained (210) information. Such erosion may be caused by prolonged exposure of the rotating component to oilfield materials during blending operations previously performed (240) to mix a fluid with a solid particle material utilizing the oilfield mixing device. As described above, estimating (230) the erosion and/or otherwise detecting (220) damage sustained by the rotating component may include determining (250) an amplitude of the obtained vibration information and estimating (260) an amount of damage sustained by the rotating component based on the determined (250) amplitude.

The method (200) may also comprise collecting (270) information relating to rotational speed and/or phase angle of the rotating component and/or another portion of the oilfield mixing device. In such implementations, detecting (220) the damage sustained by the rotating component may include estimating a location of the detected damage on the rotating component based on the collected (270) information relating to rotational speed and/or phase angle.

The method (200) may also comprise estimating (280) the remaining life of the rotating component based on the detected (220) damage sustained by the rotating component. Such estimation (280) may utilize information such as shown in Table 1 and/or the related database described above.

It is also noted that the method (200) may be performed without disassembling the rotating component from the oilfield mixing device. However, in other implementations, the method (200) may be performed after removing the rotating component from the oilfield mixing device.

Figure 7:
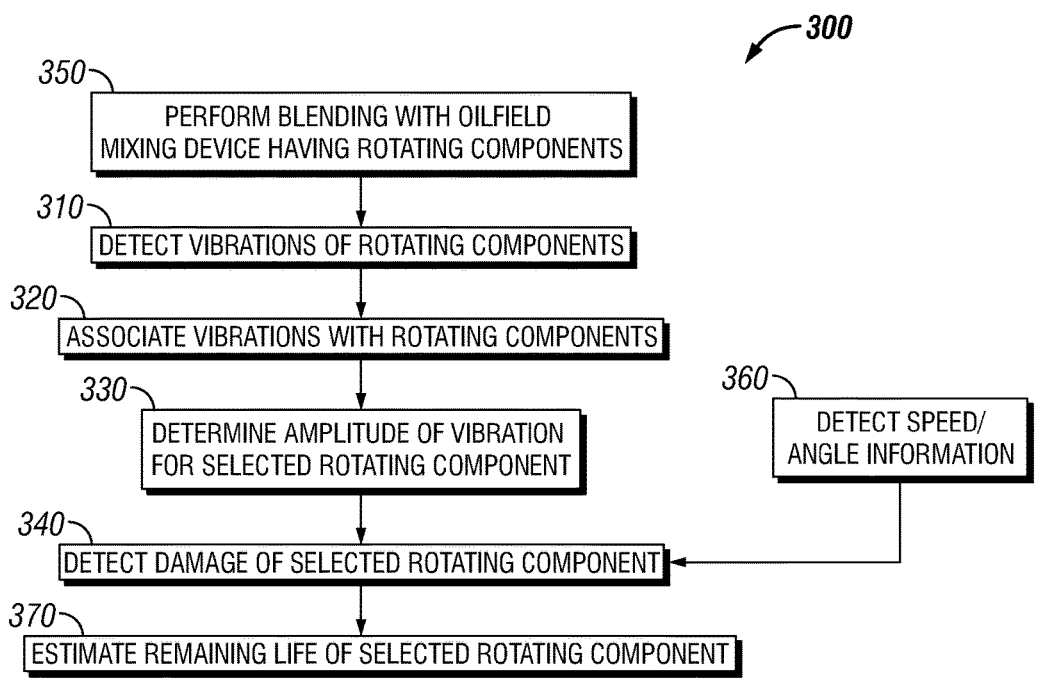
FIG. 7 is a flow-chart diagram of at least a portion of a method according to one or more aspects of the present disclosure.

FIG. 7 is a flow-chart diagram of at least a portion of another example implementation of a method (300) according to one or more aspects of the present disclosure. The method (300) may be performed utilizing at least a portion of one or more implementations of the apparatus shown in one or more of FIGS. 1-3 and/or other apparatus within the scope of the present disclosure.

The method (300) comprises detecting (310) vibrations generated by a plurality of rotating components of an oilfield mixing device. One or more aspects of the oilfield mixing device may be at least similar to those of the oilfield mixing device 10 shown in FIGS. 1 and 2, among other oilfield mixing devices within the scope of the present disclosure. For example, the rotating component be at least similar in function and/or structure to the slinger 50, the impeller 60, the drive shaft extension 45, the gear box 42 or a component thereof, the drive shaft 49, and/or the prime mover 40 shown in FIGS. 1 and 2, among other examples of rotating components within the scope of the present disclosure. Detecting (210) the vibrations generated by the rotating components may utilize apparatus that may be at least similar to one of more of the sensors 102, 104, 106, 108, 109, one or more components of the monitoring device 110, and/or other components of the monitoring system 100 shown in FIGS. 1 and 3, among other examples within the scope of the present disclosure.

The detected (310) vibrations may then be associated (320) with corresponding ones of the rotating components based on corresponding frequencies of the detected (310) vibrations. For example, the analysis described above with respect to FIGS. 4 and 5 may be utilized in associating (320) certain detected (310) vibrations with the slinger 50, associating (320) certain other detected (310) vibrations with the impeller 60, and associating (320) certain other detected (31) vibrations with the gear box 42, and similarly for the other rotating components of the oilfield mixing device.

An amplitude of the detected (310) vibrations at one of the frequencies corresponding to a selected one of the rotating components may then be determined (330). Damage sustained by the selected one of the rotating components may then be detected (340) based on the determined (330) amplitude. As described above, such as with respect to FIG. 6, detecting (340) the damage sustained by the selected one of the rotating components may include determining an amount of erosion sustained by the rotating component based on the determined (330) amplitude. As described above, such erosion may be caused by prolonged exposure to oilfield materials during blending operations previously performed (350) to mix a fluid with a solid particle material utilizing the oilfield mixing device.

The method (300) may also comprise detecting (360) rotational speed and/or phase angle of the selected one of the rotating components and/or another rotating component of the oilfield mixing device. In such implementations, detecting (340) the damage sustained by the selected one of the rotating components may include estimating a location of the detected (340) damage on the selected one of the rotating components based on the detected (360) rotational speed and/or phase angle.

The method (300) may also comprise estimating (370) the remaining life of the selected one of the rotating components based on the detected (340) damage and/or the determined (330) amplitude. Such estimation (370) may utilize information such as shown in Table 1 and/or the related database described above.

It is also noted that the method (300) may be performed without disassembling the rotating components from the oilfield mixing device. However, in other implementations, the method (300) may be performed after removing one or more of the rotating components from the oilfield mixing device.

In view of the entirety of the present disclosure, including the claims and the figures, a person having ordinary skill in the art should recognize that the present disclosure introduces an apparatus comprising: a system operable to indicate that damage has been sustained by a rotating component of an oilfield mixing device that is operable for blending oilfield materials, wherein the system comprises: a sensor connected with the oilfield mixing device and operable to generate information related to vibration of the rotating component; and a monitoring device in communication with the sensor and operable to determine an amplitude of the generated information.

The oilfield mixing device may be a vortex mixing device. The rotating component may be a slinger of the vortex mixing device.

The system may be operable to estimate an amount of erosion of the rotating component based on the determined amplitude. The erosion may be caused by prolonged exposure to the oilfield materials.

The sensor may comprise an accelerometer operable to generate the information related to vibration of the rotating component. The accelerometer may be a multi-axis accelerometer.

The determined amplitude may be indicative of an amount of damage sustained by the rotating component.

The system may be further operable to estimate remaining life of the rotating component based on the determined amplitude.

The system may further comprise a memory in communication with the monitoring device, and the system may be operable to record the generated information and the determined amplitude onto the memory.

The sensor may be a first sensor, and the system may further comprise a second sensor operable to generate information related to rotational speed and/or phase angle of the rotating component. The information generated by the first and second sensors may be indicative of: an amount of damage sustained by the rotating component due to prolonged exposure to the oilfield materials; and a location of the damage on the rotating component.

The present disclosure also introduces a method comprising: obtaining information relating to vibration of a rotating component of an oilfield mixing device, wherein the oilfield mixing device is operable to blend oilfield materials while the rotating component rotates; and detecting damage sustained by the rotating component based on the obtained information.

The oilfield mixing device may be vortex mixing device. The rotating component may be a slinger of the vortex mixing device.

Detecting damage sustained by the rotating component may comprise estimating an amount of erosion sustained by the rotating component based on the obtained information. The erosion sustained by the rotating component may be caused by prolonged exposure to the oilfield materials.

Detecting damage sustained by the rotating component may comprise: determining an amplitude of the obtained information; and estimating an amount of damage sustained by the rotating component based on the determined amplitude. The method may further comprise estimating remaining life of the rotating component based on the estimated amount of damage sustained by the rotating component. Determining the amplitude of the obtained information may comprise determining the amplitude at a frequency that distinguishes vibration of the rotating component from vibration of other components of the oilfield mixing device.

The method may further comprise: collecting information relating to rotational speed and/or phase angle of the rotating component; and estimating a location of the detected damage on the rotating component based on the collected information.

Obtaining the information relating to vibration of the rotating and detecting damage sustained by the rotating component may be performed without disassembling the rotating component from the oilfield mixing device.

The present disclosure also introduces a method comprising: detecting vibrations generated by a plurality of rotating components of an oilfield mixing device; associating the detected vibrations with corresponding ones of the plurality of rotating components based on a corresponding plurality of frequencies of the detected vibrations; determining an amplitude of the detected vibrations at one of the plurality of frequencies corresponding to a selected one of the plurality of rotating components; and detecting damage sustained by the selected one of the plurality of rotating components based on the determined amplitude.

The oilfield mixing device may be a vortex mixing device. The selected one of the plurality of rotating components may be a slinger of the vortex mixing device. Detecting damage sustained by the selected one of the plurality of rotating components may comprise determining an amount of erosion sustained by the slinger based on the determined amplitude.

The erosion may be caused by prolonged exposure to oilfield materials blended by the vortex mixing device.

The method may further comprise estimating remaining life of the selected one of the plurality of rotating components based on the determined amplitude and/or the detected damage.

The method may further comprise detecting rotational speed and/or phase angle of the selected one of the plurality of rotating components. The method may further comprise estimating a location of the detected damage on the selected one of the plurality of rotating components based on the detected rotational speed and/or phase angle.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to permit the reader to quickly ascertain the nature of the technical disclosure. It is submitted with the understanding that it will not be used to interpret or limit the scope or meaning of the claims.

What is claimed is:

1. An apparatus, comprising:
    a system operable to indicate that damage has been sustained by a rotating component of an oilfield mixing device that is operable for blending oilfield materials, wherein the system comprises:
        a first sensor connected with the oilfield mixing device and operable to generate information related to vibration of the rotating component;
        a second sensor operable to generate information related to rotational speed and/or phase angle of the rotating component; and
        a monitoring device in communication with the sensor and operable to determine an amplitude of the generated information, wherein the information generated by the first and second sensors are indicative of:
            an amount of damage sustained by the rotating component due to prolonged exposure to the oilfield materials; and
            a location of the damage on the rotating component.

2. The apparatus of claim 1 wherein the oilfield mixing device is a vortex mixing device.

3. The apparatus of claim 2 wherein the rotating component is a slinger of the vortex mixing device.

4. The apparatus of claim 1 wherein the system is operable to estimate an amount of erosion of the rotating component based on the determined amplitude.

5. The apparatus of claim 1 wherein the sensor comprises an accelerometer operable to generate the information related to vibration of the rotating component.

6. The apparatus of claim 5 wherein the accelerometer is a multi-axis accelerometer.

7. The apparatus of claim 1 wherein the sensor is a first sensor, and wherein the system further comprises a second sensor operable to generate information related to rotational speed and/or phase angle of the rotating component.

8. A method, comprising:
    obtaining information relating to vibration of a rotating component of an oilfield mixing device, wherein the oilfield mixing device is operable to blend oilfield materials while the rotating component rotates; and
    detecting damage sustained by the rotating component based on the obtained information by
    estimating an amount of erosion sustained by the rotating component based on the obtained information, and
    wherein the erosion sustained by the rotating component is caused by prolonged exposure to the oilfield materials.

9. The method of claim 8 wherein the oilfield mixing device is vortex mixing device.

10. The method of claim 9 wherein the rotating component is a slinger of the vortex mixing device.

11. The method of claim 8 wherein detecting damage sustained by the rotating component comprises:
    determining an amplitude of the obtained information; and
    estimating an amount of damage sustained by the rotating component based on the determined amplitude.

12. The method of claim 11 further comprising estimating remaining life of the rotating component based on the estimated amount of damage sustained by the rotating component.

13. The method of claim 11 wherein determining the amplitude of the obtained information comprises determining the amplitude at a frequency that distinguishes vibration of the rotating component from vibration of other components of the oilfield mixing device.

14. The method of claim 8 wherein the method further comprises:

collecting information relating to rotational speed and/or phase angle of the rotating component; and estimating a location of the detected damage on the rotating component based on the collected information.

15. The method of claim 8 wherein obtaining the information relating to vibration of the rotating and detecting damage sustained by the rotating component is performed without disassembling the rotating component from the oilfield mixing device.

16. A method, comprising:

detecting vibrations generated by a plurality of rotating components of an oilfield mixing device;

associating the detected vibrations with corresponding ones of the plurality of rotating components based on a corresponding plurality of frequencies of the detected vibrations;

determining an amplitude of the detected vibrations at one of the plurality of frequencies corresponding to a selected one of the plurality of rotating components; and detecting damage sustained by the selected one of the plurality of rotating components based on the determined amplitude;

detecting rotational speed and/or phase angle of the selected one of the plurality of rotating components; and estimating a location of the detected damage on the selected one of the plurality of rotating components based on the detected rotational speed and/or phase angle.

17. The method of claim 16 further comprising estimating remaining life of the selected one of the plurality of rotating components based on the determined amplitude and/or the detected damage.

* * * * *